(12) United States Patent
Dowdy et al.

(10) Patent No.: US 8,759,525 B2
(45) Date of Patent: Jun. 24, 2014

(54) PROCESS AND INTERMEDIATES FOR PREPARING INTEGRASE INHIBITORS

(71) Applicant: Gilead Sciences, Inc., Foster City, CA (US)

(72) Inventors: Eric Dowdy, White Rock, NM (US); Steven Pfeiffer, Camarillo, CA (US)

(73) Assignee: Gilhead Sciences, Inc., Foster City, CA (US)

( * ) Notice: Subject to any disclaimer, the term of this patent is extended or adjusted under 35 U.S.C. 154(b) by 0 days.

(21) Appl. No.: 13/868,836

(22) Filed: Apr. 23, 2013

(65) Prior Publication Data

US 2013/0253200 A1    Sep. 26, 2013

Related U.S. Application Data

(63) Continuation of application No. 13/413,518, filed on Mar. 6, 2012, now Pat. No. 8,440,831, which is a continuation of application No. 12/676,553, filed as application No. PCT/US2008/076002 on Sep. 11, 2008, now Pat. No. 8,153,801.

(60) Provisional application No. 60/971,395, filed on Sep. 11, 2007.

(51) Int. Cl.
*C07D 215/56* (2006.01)
*C07C 51/15* (2006.01)

(52) U.S. Cl.
USPC .......................................... 546/156; 562/423

(58) Field of Classification Search
None
See application file for complete search history.

(56) References Cited

U.S. PATENT DOCUMENTS

| | | | |
|---|---|---|---|
| 7,176,220 B2 | 2/2007 | Satoh et al. | |
| 7,825,252 B2 | 11/2010 | Dowdy et al. | |
| 8,153,801 B2 | 4/2012 | Dowdy et al. | |
| 8,324,244 B2 | 12/2012 | Dowdy et al. | |
| 8,383,819 B2 | 2/2013 | Matsuda et al. | |
| 8,440,831 B2 | 5/2013 | Dowdy et al. | |
| 2005/0104233 A1 | 5/2005 | Kato et al. | |
| 2008/0125594 A1 | 5/2008 | Dowdy et al. | |
| 2008/0207618 A1 | 8/2008 | Satoh et al. | |
| 2009/0036684 A1 | 2/2009 | Matsuda et al. | |
| 2009/0093467 A1 | 4/2009 | Kearney et al. | |
| 2009/0093482 A1 | 4/2009 | Kearney et al. | |
| 2009/0099366 A1 | 4/2009 | Dowdy et al. | |
| 2009/0233964 A1 | 9/2009 | Kearney et al. | |
| 2009/0318702 A1 | 12/2009 | Matsuda et al. | |
| 2010/0331331 A1 | 12/2010 | Kearney et al. | |
| 2011/0009411 A1 | 1/2011 | Kearney et al. | |
| 2012/0238758 A1 | 9/2012 | Dowdy et al. | |
| 2013/0116437 A1 | 5/2013 | Dowdy et al. | |

FOREIGN PATENT DOCUMENTS

| | | |
|---|---|---|
| EA | 200870321 A1 | 2/2009 |
| EP | 1564210 | 8/2005 |
| EP | 1582523 | 10/2005 |
| EP | 1582524 | 10/2005 |
| EP | 1 992 607 A1 | 11/2008 |
| JP | 4669040 B2 | 4/2011 |
| WO | WO 02/48113 | 6/2002 |
| WO | WO-03/043992 A1 | 5/2003 |
| WO | WO 2004/013103 | 2/2004 |
| WO | WO-2004/031159 A1 | 4/2004 |
| WO | WO 2004/046115 | 6/2004 |
| WO | WO 2005/112930 | 12/2005 |
| WO | WO 2005/113508 | 12/2005 |
| WO | WO 2005/113509 | 12/2005 |
| WO | WO 2007/063869 | 6/2007 |
| WO | WO 2007/102512 | 9/2007 |
| WO | WO 2008/033836 | 3/2008 |

OTHER PUBLICATIONS

African Regional Office Action mailed on Sep. 26, 2013, for African Regional Patent Application No. AP/P/2009/004831, filed on Sep. 11, 2007, five pages.
Chinese Office Action mailed on Nov. 11, 2013 for Chinese Patent Application No. 2008801065542, filed on Sep. 11, 2008, eleven pages.
Eurasian Office Action mailed on Dec. 19, 2013, for Eurasian Patent Application No. 2009-00441 filed on Sep. 11, 2007, fifteen pages.
International Search Report mailed on Mar. 4, 2008, for PCT Patent Application No. PCT/US2007/078157 filed on Sep. 11, 2007, three pages.
International Search Report mailed on Oct. 28, 2013, for PCT Patent Application No. PCT/US2013/053295 filed on Aug. 1, 2013, four pages.
Israeli Office Action mailed on Oct. 30, 2013 for Israeli Patent Application No. 204206, filed on Sep. 11, 2008, two pages.
European Communication mailed on May 18, 2012, for European Patent Application No. 08 830 255.9 filed on Sep. 11, 2008, four pages.
European Communication mailed on Sep. 19, 2013, for European Patent Application No. 07 842 242.5 filed on Sep. 11, 2007 four pages.
Extended European Search Report mailed on Sep. 24, 2013, for European Patent Application No. 13 174 174.6 filed on Sep. 11, 2007 eight pages.
Non-Final Office Action mailed on Oct. 1, 2013, for U.S. Appl. No. 13/619,297, filed Sep. 14, 2012, six pages.
Notice of Allowance mailed on Sep. 24, 2013 for Mexican Patent Application No. MXA/2010/002783, filed on Sep. 11, 2008, two pages.
Notice of Allowance mailed on Dec. 18, 2013 for Israeli Patent Application No. 220311, filed on Sep. 11, 2007, four pages.
Notice of Allowance mailed on Oct. 1, 2013 for Australian Patent Application No. 2008298943, filed on Sep. 11, 2008, two pages.
Sato, M. et al. (Mar. 5, 2006). "Novel HIV-1 Integrase Inhibitors Derived from Quinolone Antibiotics," *J. Medicinal Chem.* 49(5):1506-1508.

(Continued)

*Primary Examiner* — Janet L Andres
*Assistant Examiner* — Timothy R Rozof
(74) *Attorney, Agent, or Firm* — Morrison & Foerster LLP; Brandon Boss; Joel Silver

(57) ABSTRACT

The invention provides synthetic processes and synthetic intermediates that can be used to prepare 4-oxoquinolone compounds having useful integrase inhibiting properties.

6 Claims, No Drawings

(56) References Cited

OTHER PUBLICATIONS

Sorbera, L.A. et al. (Jan. 1, 2006). "GS-9137: Anti-HIV Agent HIV Integrase Inhibitor," *Drugs of the Future* 31(4):310-313.
Written Opinion of the International Searching Authority mailed on Oct. 28, 2013, for PCT Patent Application No. PCT/US2013/053295 filed on Aug. 1, 2013, six pages.
Written Opinion of the International Searching Authority mailed on Nov. 18, 2008, for PCT Patent Application No. PCT/US2008/076002 filed on Sep. 11, 2008, five pages.
Written Opinion of the International Searching Authority mailed on Mar. 4, 2008, for PCT Patent Application No. PCT/US2007/078157 filed on Sep. 11, 2007, six pages.
U.S. Appl. No. 13/956,905, filed Aug. 1, 2013, by Pcion et al.
Abdel-Aziz, Alaa A.-M. et al., "Lewis acid-promoted transformation of 2-alkoxypyridines into2-aminopyridines and their antibacterial activity. Part 2: Remarkably facile C-N bond formation", *Bioorganic and Medicinal Chemistry*, 13, 4929-4935, 2005.
Andrianov, K. A. et al., "On the reactions of trialkyl(aryl)hydrosilanes with trifuoroacetic acid", *Journal of Organometallic Chemistry*, 128, 43-55, 1977.
Bailey, William F. et al., "The Mechanism of the Lithium-Halogen Interchange Reaction: A Review of the Literature", *Journal of Organometallic Chemistry*, 352, 1-46, 1988.
Barnes David M. et al., "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram", *J. Am. Chem. Soc.*, 124, 13097-13105 and supplemental materials, 2002.
Beak Peter et al., "The reaction of n-butykkuthium with benzoic acid: is nucleophilic addition competitive with deprotonation?", *Journal of Physical Organic Chemistry*, 10, 537-541, 1997.
Bowden Sharon A. et al., "A New Approach to Rapid Parallel Development of Four Neurokinin Antagonists. Part 4. Synthesis of ZD2249 Methoxy Sulfoxide", *Organic Process Research Development*, 8, 33-44, 2004.
Da Silva, Adilson D. et al., "Biological Activity and Synthetic Methodologies for the Preparation of Fluoroquinolines, A Class of Potent Antibacterial Agents", *Current Medicinal Chemistry*, 10, 21-39, 2003.
Kato, Shinji et al., "Non-cryogenic metalation or aryl bromides bearing proton donating groups: formation of a stable magnesio-intermediate", *Tetrahedron Lett.* 43, 7315-7317, 2002.
Kursanov, D. N. et al., "Applications of Ionic Hydrogenation to Organic Synthesis", Synthesis, 633-651, 1974.
Leysen, D.C. et al., "Synthesis of Antibacterial 4-Quinoline-3-Carboxylic Acids and their Derivatives Part 1", *Die Pharmazie*, 46,485-501, 1991.
Leysen, D. C. et al., "Synthesis of Antibacterial 4-Quinoline-3-Carboxylic Acids and their Derivatives Part 2", *Die Pharmazie*, 46,557-572, 1991.
Radl, Stanislav et al., "Recent Advances in the Synthesis of Antibacterial Quinolones", *Heterocycles*, 34-11, 2143-2177, 1992.
Smith et al., "March's Advanced Organic Chemistry: Reactions, Mechanisms, and Structure", *Wiley-Interscience Publication, John Wiley & Son*, p. 564, 5th ed., © 2001.
International Search Report and Written Opinion of the International Searching Authority, PCT/US2008/076002, Nov. 18, 2008.
Non-Final Office Action, U.S. Appl. No. 12/676,553, Apr. 27, 2011.
Restriction Requirement, U.S. Appl. No. 12/208,952, Jun. 28, 2011.

PROCESS AND INTERMEDIATES FOR PREPARING INTEGRASE INHIBITORS

CROSS-REFERENCE TO RELATED APPLICATIONS

This application is a Continuation of U.S. patent application Ser. No. 13/413,518 (Now U.S. Pat. No. 8,440,831), filed Mar. 6, 2012, which is a Continuation of U.S. patent application Ser. No. 12/676,553 (U.S. Pat. No. 8,153,801), which is the National Stage of International Patent Application of PCT/US2008/076002, filed Sep. 11, 2008, which claims priority to and the benefit of U.S. Provisional Application Ser. No. 60/971,395, filed Sep. 11, 2007, each of which is hereby incorporated by reference in the present disclosure in its entirety.

BACKGROUND OF THE INVENTION

International Patent Application Publication Number WO 2004/046115 provides certain 4-oxoquinolone compounds that are useful as HIV integrase inhibitors. The compounds are reported to be useful as anti-HIV agents.

International Patent Application Publication Number WO 2005/113508 provides certain specific crystalline forms of one of these 4-oxoquinolone compounds, 6-(3-chloro-2-fluorobenzyl)-1-[(S)-1-hydroxymethyl-2-methylpropyl]-7-methoxy-4-oxo-1,4-dihydroquinolone-3-carboxylic acid. The specific crystalline forms are reported to have superior physical and chemical stability compared to other physical forms of the compound.

There is currently a need for improved methods for preparing the 4-oxoquinolone compounds reported in International Patent Application Publication Number WO 2004/046115 and in International Patent Application Publication Number WO 2005/113508. In particular, there is a need for new synthetic methods that are simpler or less expensive to carry out, that provide an increased yield, or that eliminate the use of toxic or costly reagents.

SUMMARY OF THE INVENTION

The present invention provides new synthetic processes and synthetic intermediates that are useful for preparing the 4-oxoquinolone compounds reported in International Patent Application Publication Number WO 2004/046115 and in International Patent Application Publication Number WO 2005/113508.

Accordingly, in one embodiment, the present invention provides a method for preparing a compound of formula 10

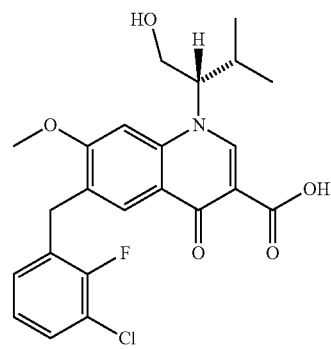

10 or a pharmaceutically acceptable salt thereof, in which a compound of formula 4

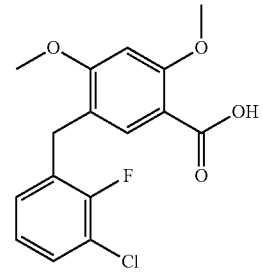

4 or a salt thereof is prepared and converted into a compound of formula 10, characterized in that the compound of formula 4 is prepared from a compound of formula 15

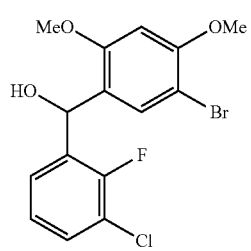

15 or a salt thereof, by the steps of replacing the bromine atom with a carboxyl group, and replacing the hydroxyl group with a hydrogen atom.

In another embodiment the invention provides a compound of formula 15:

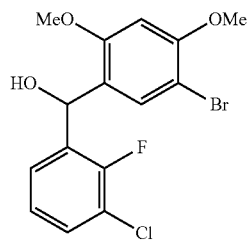

15 or a salt thereof.

In another embodiment the invention provides a method for preparing a compound of formula 15:

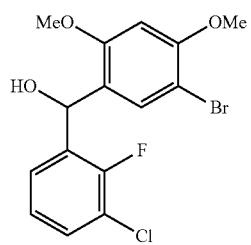

15 or a salt thereof comprising converting a corresponding compound of formula 14:

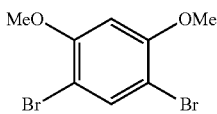

14 to the compound of formula 15 or the salt thereof.

In another embodiment the invention provides a compound of formula 15a:

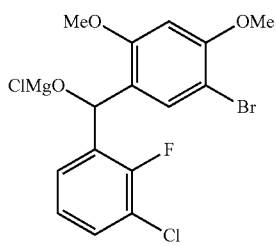

15a that is useful as an intermediate for preparing the 4-oxo-quinone compounds.

In another embodiment the invention provides a compound of formula 16:

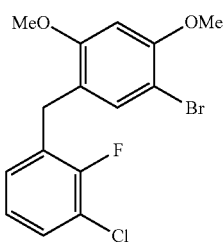

16 that is useful as an intermediate for preparing the 4-oxo-quinone compounds.

The invention also provides other synthetic processes and synthetic intermediates disclosed herein that are useful for preparing the 4-oxoquinone compounds.

DETAILED DESCRIPTION

The following definitions are used, unless otherwise described: halo is fluoro, chloro, bromo, or iodo. Alkyl denotes both straight and branched groups, but reference to an individual radical such as propyl embraces only the straight chain radical, a branched chain isomer such as isopropyl being specifically referred to.

It will be appreciated by those skilled in the art that a compound having a chiral center may exist in and be isolated in optically active and racemic forms. Some compounds may exhibit polymorphism. It is to be understood that the present invention encompasses processes for preparing any racemic, optically-active, polymorphic, tautomeric, or stereoisomeric form, or mixtures thereof, of a compound described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Specific and preferred values listed below for radicals, substituents, and ranges, are for illustration only; they do not exclude other defined values or other values within defined ranges for the radicals and substituents.

Specifically, $C_1$-$C_6$alkyl can be methyl, ethyl, propyl, iso-propyl, butyl, iso-butyl, sec-butyl, pentyl, 3-pentyl, or hexyl.

A specific value for $R_a$ is methyl.
A specific value for $R_b$ is methyl.
A specific value for $R_c$ is 1-imidazolyl.
A specific value for R is ethyl.

In one embodiment, the compound of formula 4 or a salt thereof is prepared by metalating the compound of formula 15 or a salt thereof and treating with carbon dioxide to provide the compound of formula 3:

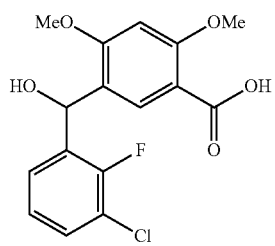

3 or a salt thereof, and then converting the compound of formula 3 into a compound of formula 4.

The compound of formula 15 or a salt thereof may be, for example, a salt of formula 15a

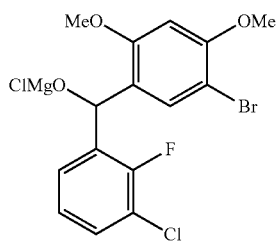

15a

In another embodiment, the compound of formula 15 is converted into a compound of formula 16

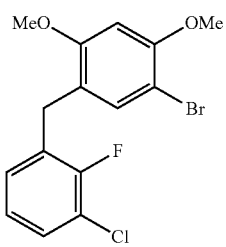

16 which is then metalated and treated with carbon dioxide to afford a compound of formula 4.

It will be appreciated that the step of replacing the bromine atom with a carboxyl group is a carboxylation. This step may conveniently be effected by metalation, for example, by treatment with isopropylmagnesium chloride or isopropylmagnesium chloride lithium chloride complex, followed by treatment with carbon dioxide.

It will also be appreciated that the step of replacing the hydroxyl group with a hydrogen atom is a dehydroxylation. This step may be effected by treatment with a trialkylsilane, such as triethylsilane, conveniently in the presence of trifluoroacetic acid.

In another embodiment of the invention the compound of formula 15 or a salt thereof is converted to a compound of formula 3:

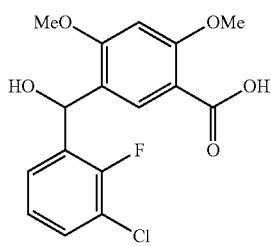

3 or a salt thereof. For example, the compound of formula 15 or a salt thereof can be converted to the compound of formula 3 or a salt thereof by metalating the compound of formula 15 or the salt thereof (e.g. by treatment with isopropylmagnesium chloride) and treating with carbon dioxide to provide the compound of formula 3 or the salt thereof.

In another embodiment of the invention the compound of formula 3 or the salt thereof is converted to a compound of formula 4:

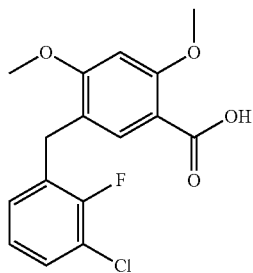

4 or a salt thereof.

In another embodiment of the invention the compound of formula 4 is converted to a compound of formula 5':

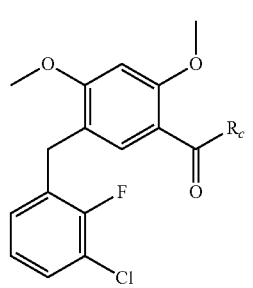

5' or a salt thereof, wherein $R_c$ is a leaving group (such as halo or 1-imidazolyl). The carboxylic acid functional group of Compound 4 can be converted to an activated species, for example an acid chloride or an acyl imidazolide (Compound 5') by treatment with a suitable reagent, such as, for example, thionyl chloride, oxalyl chloride, cyanuric chloride or 1,1'-carbonyldiimidazole in a suitable solvent (e.g., toluene or tetrahydrofuran). Any suitable leaving group $R_c$ can be incorporated into the molecule, provided the compound of formula 5' can be subsequently converted to a compound of formula 6. The reaction can conveniently be carried out using about 1 equivalent of 1,1'-carbonyldiimidazole in tetrahydrofuran. In one embodiment, the compound of formula 5' is a compound of formula 5a.

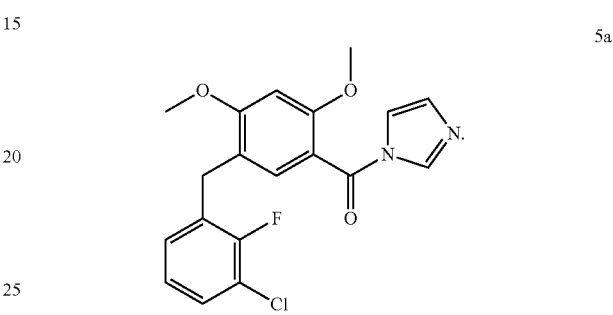

5a

The compound of formula 4 may be converted to the compound of formula 5a by treatment with 1,1'-carbonyldiimidazole.

In another embodiment of the invention a compound of formula 5' or a salt thereof, can be converted to a compound of formula 6:

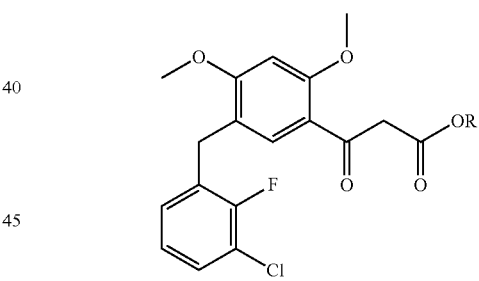

6 or a salt thereof, wherein R is $C_1$-$C_6$alkyl. In one embodiment, the compound of formula 5' is converted to the compound of formula 6 by treatment with the corresponding mono-alkylmalonate salt. An example of a mono-alkylmalonate salt is potassium monoethylmalonate. For example, a compound of formula 5' can be combined with about 1 to 5 equivalents of a monoalkyl malonate salt and about 1 to 5 equivalents of a magnesium salt in a suitable solvent. Conveniently, a compound of formula 5' can be combined with about 1.7 equivalents of potassium monoethyl malonate and about 1.5 equivalents of magnesium chloride. A suitable base, for example triethylamine or imidazole, can be added to the reaction. The reaction can conveniently be carried out at an elevated temperature (e.g., about 100±50° C.) and monitored for completion by any suitable technique (e.g., by HPLC). Upon completion of the reaction, Compound 6 can be isolated using any suitable technique (e.g., by chromatography or crystallization).

In another embodiment of the invention the compound of formula 6 or a salt thereof, can be converted to a corresponding compound of formula 7:

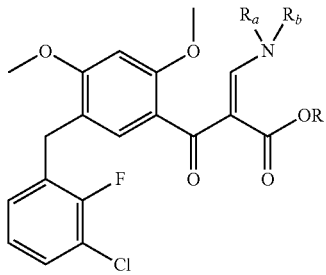

wherein $R_a$ and $R_b$ are each independently $C_1$-$C_6$alkyl; and R is $C_1$-$C_6$alkyl. Compound 6 can be converted to an activated alkylidene analog, such as Compound 7, by treatment with a formate group donor such as a dimethylformamide dialkyl acetal (e.g., dimethylformamide dimethyl acetal) or a trialkylorthoformate. The reaction can be carried out at elevated temperature (e.g., about 100±50° C.). This reaction may be accelerated by the addition of an acid catalyst, such as, for example, an alkanoic acid, a benzoic acid, a sulfonic acid or a mineral acid. About 500 ppm to 1% acetic acid can conveniently be used. The progress of the reaction can be monitored by any suitable technique (e.g., by HPLC). Compound 7 can be isolated or it can be used directly to prepare a compound of formula 8 as described below.

In another embodiment of the invention the compound of formula 7 can be converted to a corresponding compound of formula 8:

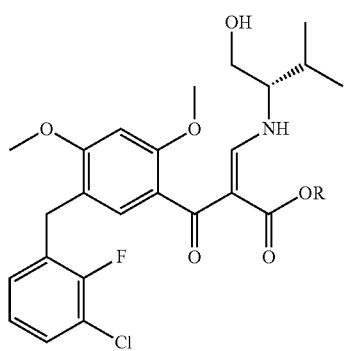

wherein R is $C_1$-$C_6$alkyl. Compound 7 can be combined with (S)-2-amino-3-methyl-1-butanol (S-Valinol, about 1.1 equivalents) to provide compound 8. The progress of the reaction can be monitored by any suitable technique (e.g., by HPLC). The compound of formula 8 can be isolated or used directly to prepare a compound of formula 9 as described below.

In another embodiment, the invention provides a method for preparing a compound of formula 9:

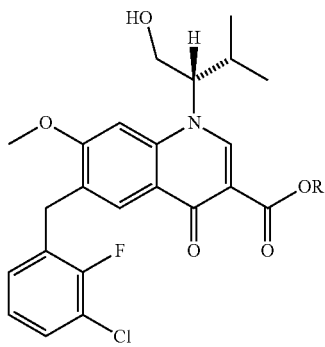

wherein R is $C_1$-$C_6$alkyl, comprising cyclizing a corresponding compound of formula 8:

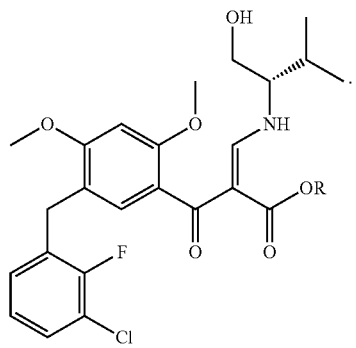

Compound 8 can be cyclized to provide Compound 9 by treatment with a silylating reagent (e.g., N,O-bis(trimethylsilyl)acetamide, N,O-bis(trimethylsilyl)trifluoroacetamide or hexamethyldisilazane). The reaction can be conducted in a polar aprotic solvent (e.g., dimethylformamide, dimethylacetamide, N-methylpyrrolidinone or acetonitrile). A salt (e.g., potassium chloride, lithium chloride, sodium chloride or magnesium chloride) can be added to accelerate the reaction. Typically, about 0.5 equivalents of a salt such as potassium chloride is added. The reaction may be conducted at elevated temperature (e.g., a temperature of about 100±20° C.) if necessary to obtain a convenient reaction time. The progress of the reaction can be monitored by any suitable technique (e.g., by HPLC). During the workup, an acid can be used to hydrolyze any silyl ethers that form due to reaction of the silylating reagent with the alcohol moiety of compound 8. Typical acids include mineral acids, sulfonic acids, or alkanoic acids. One specific acid that can be used is aqueous hydrochloric acid. Upon completion of the hydrolysis, Compound 9 can be isolated by any suitable method (e.g., by chromatography or by crystallization). In the above conversion, the silating reagent transiently protects the alcohol and is subsequently removed. This eliminates the need for separate protection and deprotection steps, thereby increasing the efficiency of the conversion.

In another embodiment of the invention the compound of formula 9 is converted to a compound of formula 10:

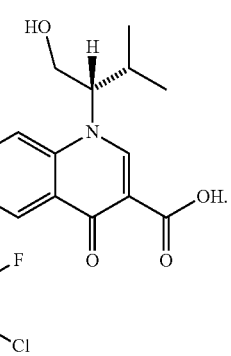

Compound 9 can be converted to Compound 10 by treatment with a suitable base (e.g., potassium hydroxide, sodium hydroxide or lithium hydroxide). For example, about 1.3 equivalents of potassium hydroxide can conveniently be used. This reaction may be conducted in any suitable solvent, such as, for example, tetrahydrofuran, methanol, ethanol or isopropanol, or a mixture thereof. The solvent can also include water. A mixture of isopropanol and water can conveniently be used. The progress of the reaction can be monitored by any suitable technique (e.g., by HPLC). The initially formed carboxylate salt can be neutralized by treatment with an acid (e.g., hydrochloric acid or acetic acid). For example, about 1.5 equivalents of acetic acid can conveniently be used. Following neutralization, Compound 10 can be isolated using any suitable technique (e.g., by chromatography or crystallization).

In another embodiment of the invention the compound of formula 10 can be crystallized by adding a seed crystal to a solution that comprises the compound of formula 10. International Patent Application Publication Number WO 2005/113508 provides certain specific crystalline forms of 6-(3-chloro-2-fluorobenzyl)-1-[(S)-1-hydroxymethyl-2-methylpropyl]-7-methoxy-4-oxo-1,4-dihydroquinolone-3-carboxylic acid. The entire contents of International Patent Application Publication Number WO 2005/113508 is incorporated herein by reference (in particular, see pages 12-62 therein). The specific crystalline forms are identified therein as Crystal Form II and Crystal Form III. Crystal form II has an X-ray powder diffraction pattern having characteristic diffraction peaks at diffraction angles 2θ(°) of 6.56, 13.20, 19.86, 20.84, 21.22, and 25.22 as measured by an X-ray powder diffractometer. Crystal form III has an X-ray powder diffraction pattern having characteristic diffraction peaks at diffraction angles 2θ(°) of 8.54, 14.02, 15.68, 17.06, 17.24, 24.16, and 25.74 as measured by an X-ray powder diffractometer. International Patent Application Publication Number WO 2005/113508 also describes how to prepare a crystalline form of 6-(3-chloro-2-fluorobenzyl)-1-[(S)-1-hydroxymethyl-2methylpropyl]-7-methoxy-4-oxo-1,4-dihydroquinolone-3-carboxylic acid that have an extrapolated onset temperature of about 162.1° C., as well as how to prepare a seed crystal having a purity of crystal of not less than about 70%. Accordingly, seed crystals of 6-(3-chloro-2-fluorobenzyl)-1-[(S)-1-hydroxymethyl-2-methylpropyl]-7-methoxy-4-oxo-1,4-dihydroquinolone-3-carb oxylic acid can optionally be prepared as described in International Patent Application Publication Number WO 2005/113508. Advantageously, the process illustrated in Scheme I below provides a crude mixture of Compound 10 that can be directly crystallized to provide Crystal Form III without additional purification (e.g. without the prior formation of another polymorph such as Crystal Form II, or without some other form of prior purification), see Example 6 below.

In cases where compounds identified herein are sufficiently basic or acidic to form stable acid or base salts, the invention also provides salts of such compounds. Such salts may be useful as intermediates, for example, for purifying such compounds. Examples of useful salts include organic acid addition salts formed with acids, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording an anion. Alkali metal (for example, sodium, potassium, or lithium) or alkaline earth metal (for example calcium or magnesium) salts of carboxylic acids, for example, can also be made.

The invention will now be illustrated by the following non-limiting Examples.

An integrase inhibitor of formula 10 can be prepared as illustrated in the following Scheme 1.

SCHEME 1

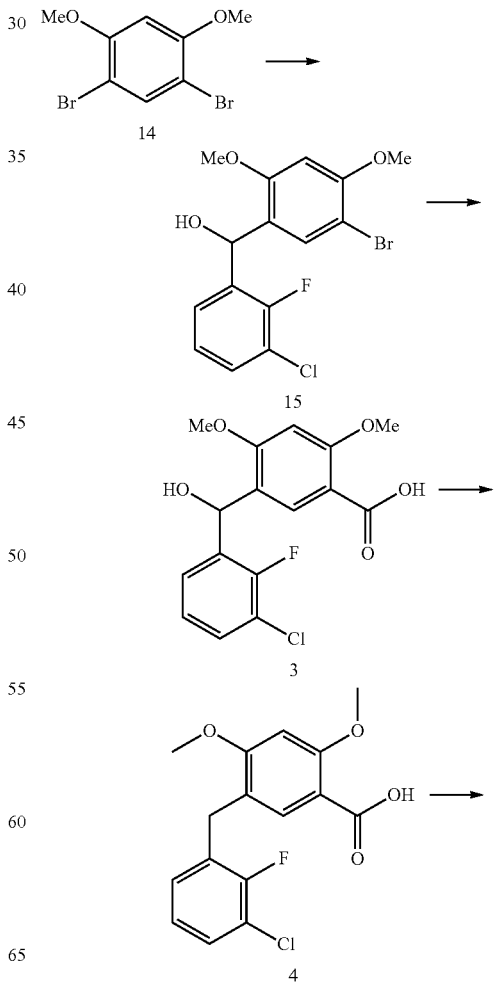

-continued

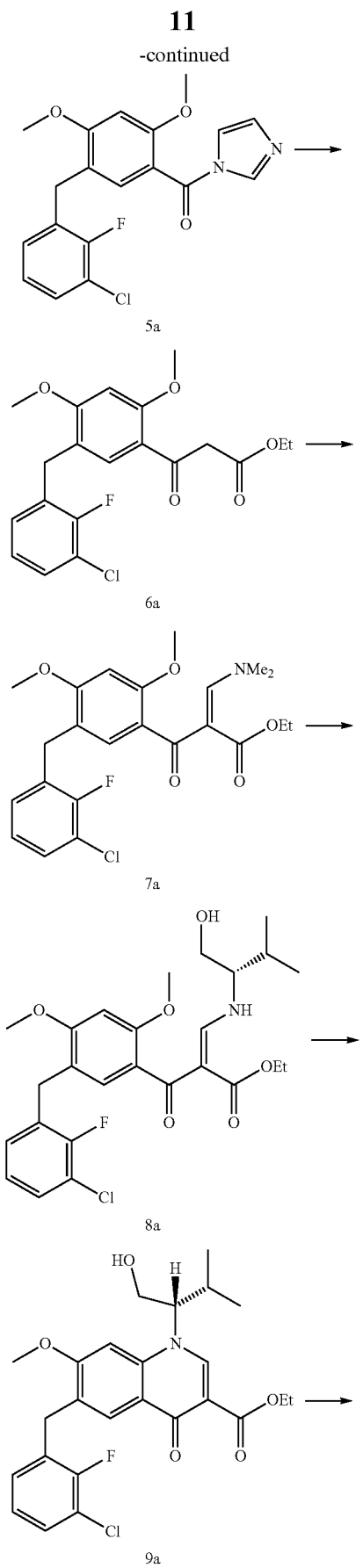

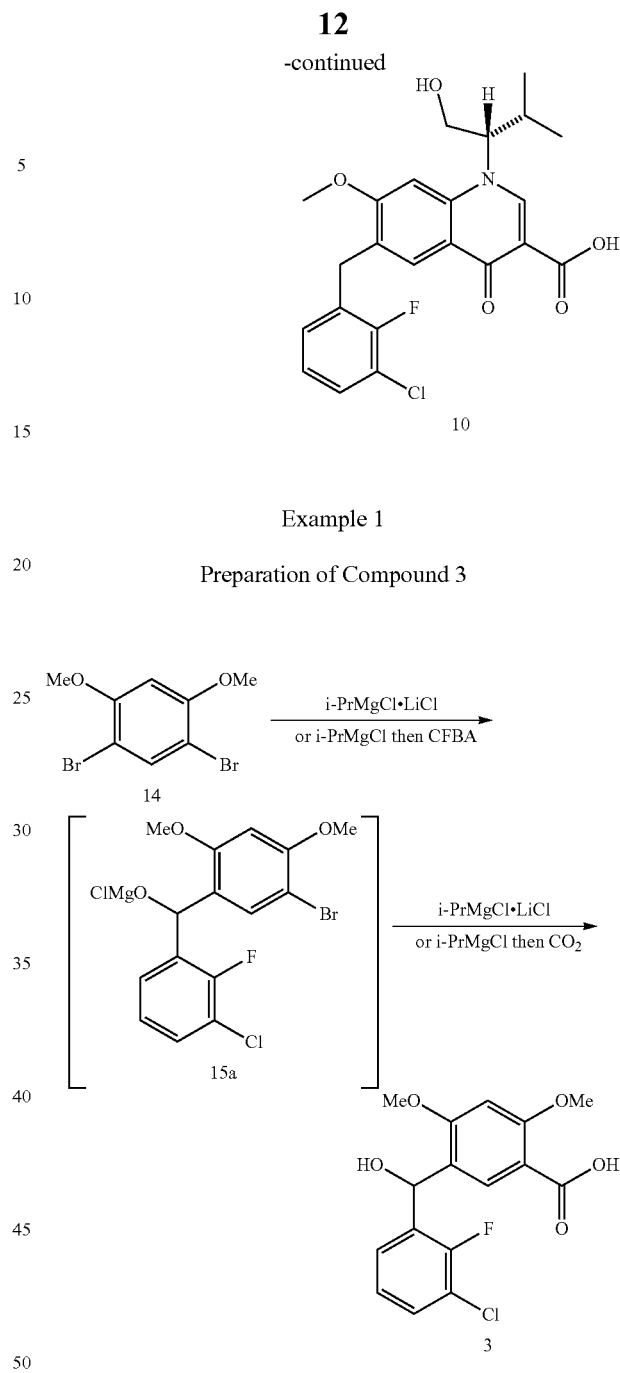

Example 1

Preparation of Compound 3

Compound 14 (10 g) was combined with 28 mL of THF and 9 mL of bisdimethylaminoethyl ether before being cooled to 0° C. Isopropylmagnesium chloride (22.9 mL of a 2.07 M solution in THF) was added and the mixture was allowed to warm to room temperature overnight. Additional isopropylmagnesium chloride (5 mL) was added to improve conversion before 3-chloro-2-fluorobenzaldehyde (4.4 mL) was added. After stirring at ambient temperature for 2 hours 38.6 g of a 14 wt % THF solution of isopropylmagnesium chloride lithium chloride complex was added. After stirring overnight at ambient temperature $CO_2$ gas was bubbled into the reaction mixture. When conversion was complete the reaction was quenched to pH <3 with 2 M hydrochloric acid. The phases were separated and the organic phase was extracted with ethyl acetate. The combined organic layers were washed with saturated aqueous sodium chloride. The organic phase was concentrated and the product precipitated by the addition of MTBE. The slurry was filtered and the product air dried to yield Compound 3: $^1$H NMR (DMSO-$d_6$, 400 MHz) δ 12.15 (br s, 1H), 7.81 (s, 1H), 7.42 (t, J=7.2 Hz, 1H), 7.26 (t, J=6.8 Hz, 1H), 7.15 (t, J=7.8 Hz, 1H), 6.77 (s, 1H), 6.09 (d, J=4.7 Hz, 1H), 5.90 (d, J=4.9 Hz, 1H), 3.84 (s, 3H), 3.80 (s, 3H).

Example 2

Preparation of Compound 4

Triethylsilane (6.83 g) was added to trifluoroacetic acid (33.13 g) that had been pre-cooled in an ice bath. Compound 3 (10 g) was added to the mixture keeping the temperature below 15° C. After stirring for 2 h MTBE was added to precipitate the product. The slurry was filtered and the product washed with additional MTBE. After drying, 9.12 g of Compound 4 was isolated: $^1$H NMR (DMSO-$d_6$, 400 MHz) δ 12.11 (br s, 1H), 7.47 (s, 1H), 7.42-7.38 (m, 1H), 7.14-7.08 (m, 2H), 6.67 (s, 1H), 3.87-3.84 (m, 8H).

Alternatively, Compound 4 can be prepared as follows.

Triethylsilane (7.50 g) was added to trifluoroacetic acid (49.02 g) that had been pre-cooled in an ice bath. Compound 3 (14.65 g) was added to the mixture keeping the temperature below 15° C. After stirring for 1 h a solution of 17.63 g sodium acetate in 147 mL methanol was added. The mixture was heated to reflux for 3 hours then cooled to 0° C. The slurry was filtered and the product washed with additional methanol. After drying 12.3 g of Compound 4 (89.7% yield) was isolated: $^1$H NMR (DMSO-$d_6$, 400 MHz) δ 12.11 (br s, 1H), 7.47 (s, 1H), 7.42-7.38 (m, 1H), 7.14-7.08 (m, 2H), 6.67 (s, 1H), 3.87-3.84 (m, 8H).

Example 3

Preparation of Compound 5a

Imidazole (0.42 g) and 1,1'-carbonyldiimidazole (5.49 g) were slurried in 30 mL of THF at ambient temperature. Compound 4 (10 g) was added in one portion and the mixture was stirred at ambient temperature until the reaction was complete by HPLC. The resulting slurry was filtered and the solids washed with MTBE. The solids were dried to yield Compound 5a: $^1$H NMR (DMSO-$d_6$, 400 MHz) δ 7.99 (s, 1H), 7.52 (s, 1H), 7.41-7.38 (m, 1H), 7.30 (s, 1H), 7.12-7.08 (m, 2H), 7.04 (s, 1H), 6.81 (s, 1H), 3.91 (s, 2H), 3.90 (s, 3H), 3.79 (s, 3H).

Example 4

Preparation of Compound 6a

Imidazole (0.42 g) and 1,1'-carbonyldiimidazole (5.49 g) were slurried in 30 mL of THF at ambient temperature. Compound 5a (10 g) was added in one portion and the mixture was stirred at ambient temperature for 4 hours to form a slurry of compound 5a. In a separate flask, 8.91 g of potassium monoethyl malonate was slurried in 40 mL of THF. Magnesium chloride (4.40 g) was added and the resulting slurry was warmed to 55° C. for 90 minutes. The slurry of Compound 5a was transferred to the magnesium chloride/potassium monoethyl malonate mixture and stirred at 55° C. overnight. The mixture was then cooled to room temperature and quenched by the dropwise addition of 80 mL of 28 wt % aqueous $H_3PO_4$. The phases were separated and the organic phase was washed successively with aqueous $NaHSO_4$, $KHCO_3$ and NaCl solutions. The organic phase was concentrated to an oil and then coevaporated with ethanol. The resulting solid was dissolved in 30 mL ethanol and 6 mL water. Compound 6a was crystallized by cooling. The solid was isolated by filtration and the product was washed with aqueous ethanol. After drying Compound 6a was obtained: $^1$H NMR (DMSO-$d_6$, 400 MHz) δ 7.51 (s, 1H), 7.42-7.38 (m, 1H), 7.12-7.10 (m, 2H), 6.70 (s, 1H), 4.06 (q, J=7.0 Hz, 2H), 3.89 (s, 8H), 3.81 (s, 2H), 1.15 (t, J=7.0 Hz, 3H).

Alternatively, Compound 6a can be prepared as follows.

Carbonyldiimidazole (10.99 g) was slurried in 60 mL of THF at ambient temperature. Compound 4 (20 g) was added in one portion and the mixture was stirred at ambient temperature for 30 min to form a slurry of compound 5. In a separate flask 15.72 g of potassium monoethyl malonate was slurried in 100 mL of THF. Magnesium chloride (6.45 g) was added and the resulting slurry was warmed to 55° C. for 5 hours. The slurry of Compound 5 was transferred to the magnesium chloride/potassium monoethyl malonate mixture and stirred at 55° C. overnight. The mixture was then cooled to room temperature and quenched onto 120 mL of 28 wt % aqueous $H_3PO_4$. The phases were separated and the organic phase was washed successively with aqueous $KHCO_3$ and NaCl solutions. The organic phase was concentrated to an oil and then coevaporated with ethanol. The resulting solid was dissolved in 100 mL ethanol and 12 mL water. Compound 6a was crystallized by cooling. The solid was isolated by filtration and the product was washed with aqueous ethanol. After drying 21.74 g Compound 6a (89% yield) was obtained: $^1$H NMR (DMSO-$d_6$, 400 MHz) δ 7.51 (s, 1H), 7.42-7.38 (m, 1H), 7.12-7.10 (m, 2H), 6.70 (s, 1H), 4.06 (q, J=7.0 Hz, 2H), 3.89 (s, 8H), 3.81 (s, 2H), 1.15 (t, J=7.0 Hz, 3H).

Example 5

Preparation of Compound 9a

Compound 6a (20 g) was stirred with 6.6 g dimethylformamide dimethyl acetal, 66 g toluene and 0.08 g glacial acetic acid. The mixture was warmed to 90° C. for 4 hours. The mixture was then cooled to ambient temperature and 5.8 g (S)-2-amino-3-methyl-1-butanol was added. The mixture was stirred at ambient temperature for 1 hour before being concentrated to a thick oil. Dimethylformamide (36 g), potassium chloride (1.8 g) and bis(trimethylsilyl)acetamide (29.6 g) were added and the mixture was warmed to 90° C. for 1 h. The mixture was cooled to room temperature and diluted with 200 g dichloromethane. Dilute hydrochloride acid (44 g, about 1N) was added and the mixture stirred at ambient temperature for 20 min. The phases were separated and the organic phase was washed successively with water, aqueous sodium bicarbonate and water. The solvent was exchanged to acetonitrile and the volume was adjusted to 160 mL. The mixture was heated to clarity, cooled slightly, seeded and cooled to crystallize Compound 9a. The product was isolated by filtration and washed with additional cold acetonitrile. Vacuum drying afforded Compound 9a: $^1$H NMR (DMSO-$d_6$, 400 MHz) δ 8.61 (s, 1H), 7.86 (s, 1H), 7.45 (t, J=7.4 Hz, 1H), 7.26 (s, 1H), 7.23-7.14 (m, 2H), 5.10 (br s, 1H), 4.62 (br s, 1H), 4.18 (q, J=7.0 Hz, 2H), 4.03 (s, 2H), 3.96 (s, 3H), 3.92-3.84 (m, 1H), 3.78-3.75 (m, 1H), 2.28 (br s, 1H), 1.24 (t, J=7.0 Hz, 3H), 1.12 (d, J=6.4 Hz, 3H), 0.72 (d, J=6.4 Hz, 3H).

Alternatively, Compound 9a can be prepared as follows.

Compound 6a (50 g) was stirred with 17.5 g dimethylformamide dimethyl acetal, 90 g DMF and 0.2 g glacial acetic acid. The mixture was warmed to 65° C. for 3 hours. The mixture was then cooled to ambient temperature and 14.5 g (S)-2-amino-3-methyl-1-butanol and 25 g toluene were added. The mixture was stirred at ambient temperature overnight before being concentrated by distillation. Potassium chloride (4.5 g) and bis(trimethylsilyl)acetamide (80.2 g) were added and the mixture was warmed to 90° C. for 2 h. The mixture was cooled to room temperature and diluted with 250 g dichloromethane. Dilute hydrochloride acid (110 g of ~1N) was added and the mixture stirred at ambient temperature for 30 min. The phases were separated and the organic phase was washed successively with water, aqueous sodium bicarbonate and water. The solvent was exchanged to acetonitrile by distillation. The mixture was heated to clarity, cooled slightly, seeded and cooled to crystallize Compound 9a. The product was isolated by filtration and washed with additional cold acetonitrile. Vacuum drying afforded 48.7 g (81% yield) of Compound 9a: $^1$H NMR (DMSO-d$_6$, 400 MHz) δ 8.61 (s, 1H), 7.86 (s, 1H), 7.45 (t, J=7.4 Hz, 1H), 7.26 (s, 1H), 7.23-7.14 (m, 2H), 5.10 (br s, 1H), 4.62 (br s, 1H), 4.18 (q, J=7.0 Hz, 2H), 4.03 (s, 2H), 3.96 (s, 3H), 3.92-3.84 (m, 1H), 3.78-3.75 (m, 1H), 2.28 (br s, 1H), 1.24 (t, J=7.0 Hz, 3H), 1.12 (d, J=6.4 Hz, 3H), 0.72 (d, J=6.4 Hz, 3H).

Example 6

Preparation of Compound 10

Compound 9a (6.02 g) was slurried in 36 mL isopropanol and 24 mL of water. Aqueous potassium hydroxide (2.04 g of 45 wt % solution) was added and the mixture warmed to 40° C. After 3 hours 1.13 g glacial acetic acid was added the mixture seeded with 10 mg of Compound 10. The mixture was cooled in an ice bath for 2 hours and the solid was isolated by filtration. The cake was washed with aqueous isopropanol and dried to give Compound 10: $^1$H NMR (DMSO-d$_6$, 400 MHz) δ 15.42 (s, 1H), 8.87 (s, 1H), 8.02 (s, 1H), 7.48-7.45 (m, 2H), 7.23 (t, J=6.8 Hz, 1H), 7.17 (t, J=7.8 Hz, 1H), 5.18 (br s, 1H), 4.86 (br s, 1H), 4.10 (s, 2H), 4.02 (s, 3H), 3.97-3.96 (m, 1H), 3.79-3.76 (m, 1H), 2.36 (br s, 1H), 1.14 (d, J=6.3 Hz, 3H), 0.71 (d, J=6.3 Hz, 3H).

Alternatively, Compound 10 can be prepared from Compound 4 as described in the following illustrative Examples 7-9.

Example 7

Preparation of a Compound of Formula 6a

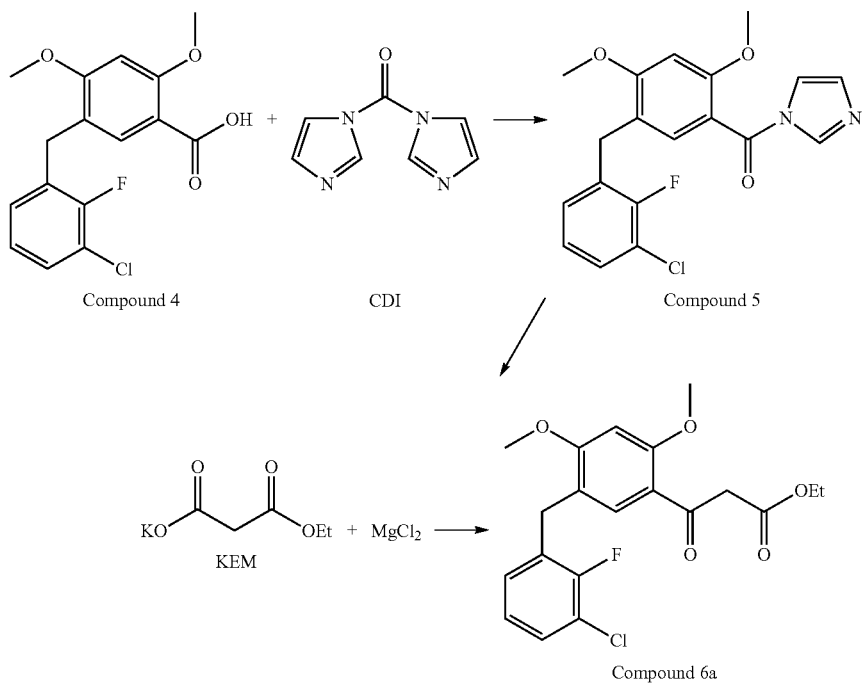

Carbonyldiimidazole and imidazole are combined with anhydrous tetrahydrofuran. Compound 4 is added to this mixture to form Compound 5 and the reaction is monitored by HPLC. In a separate reactor potassium monoethylmalonate is combined with tetrahydrofuran before anhydrous magnesium chloride is added while maintaining the temperature NMT 30° C. The resulting slurry is warmed to 50° C. and held for at least two hours before the Compound 5 mixture is added. The reaction is monitored by HPLC. Once the formation of Compound 5 is complete, the mixture is cooled to 18 to 25° C. and added to aqueous phosphoric acid to quench. The organic phase is washed with aqueous sodium bisulfate, brine, potassium bicarbonate and brine solutions before being polish filtered. The solvent is exchanged for anhydrous ethanol. Water is added and the mixture is warmed to dissolve solids, cooled to about 40° C., seeded with Compound 6a and cooled to 0 to 5° C. The product is filtered, washed with cold aqueous ethanol and dried at NMT 40° C. to yield Compound 6a.

| Material | M.W. | Wt. Ratio | Mole Ratio |
|---|---|---|---|
| Compound 4 | 324.73 | 1.000 | 1.00 |
| THF | 72.11 | 7.11 | |
| Imidazole | 68.08 | 0.042 | 0.20 |

-continued

| Material | M.W. | Wt. Ratio | Mole Ratio |
| --- | --- | --- | --- |
| CDI | 162.15 | 0.55 | 1.10 |
| KEM | 170.2 | 0.89 | 1.70 |
| MgCl$_2$ | 95.21 | 0.44 | 1.50 |
| H$_3$PO$_4$ (85 wt %) | 98.00 | 2.3 | |
| NaHSO$_4$ | 120.06 | 0.24 | |
| KHCO$_3$ | 100.12 | 0.50 | |
| NaCl | 58.44 | 0.48 | |
| SDA 2B-2 EtOH (0.5% heptane) | 46.07 | ~10 kg | |

Procedure:

1. Charge 0.55 kg CDI and 0.042 kg imidazole to reactor 1.
2. Charge 2.67 kg THF to reactor 1 and agitate to form a slurry.
3. Charge 1.00 kg Compound 4 to reactor 1 in portions to moderate the CO$_2$ offgas. This addition is endothermic
4. Charge 0.89 kg KEM to reactor 2.
5. Charge 4.45 kg THF to reactor 2 and agitate to form a slurry.
6. Charge 0.44 kg MgCl$_2$ to reactor 2 (can be added in portions to moderate exotherm).
7. Warm the contents of reactor 2 to 50° C. and agitate at that temperature for at least two hours.
8. Transfer the contents of reactor 1 to reactor 2. Mixture will become thick temporarily if transferred very rapidly.
9. Agitate the contents of reactor 2 for at least 12 hours at 50° C.
10. Cool the slurry to ambient temperature.
11. Quench the reaction by transferring the reaction mixture onto 7.0 kg of 28 wt % aqueous H$_3$PO$_4$ (2.3 kg 85 wt % H$_3$PO$_4$ dissolved in 4.7 kg H$_2$O). This addition is exothermic. Final pH of aqueous layer should be 1-2.
12. Wash the organic (top) phase with 1.2 kg of 20 wt % aqueous NaHSO$_4$ (0.24 kg of NaHSO$_4$ dissolved in 0.96 kg H$_2$O). Final pH of aqueous layer should be 1-2.
13. Wash the organic (top) phase with 1.2 kg of 20 wt % aqueous NaCl (0.24 kg of NaCl dissolved in 0.96 kg H$_2$O)
14. Wash the organic (top) phase with 5.0 kg of 10 wt % aqueous KHCO$_3$ (0.50 kg of KHCO$_3$ dissolved in 4.5 kg H$_2$O). Final pH of aqueous layer should be 8-10.
15. Wash the organic (top) phase with 1.2 kg of 20 wt % aqueous NaCl (0.24 kg of NaCl dissolved in 0.96 kg H$_2$O). Final pH of aqueous layer should be 7-9.
16. Concentrate the organic phase and exchange the solvent to EtOH.
17. Adjust the concentration to ~3.5 L/kg input.
18. Charge 0.6 volumes of water.
19. Warm 70-80° C. to form a clear solution.
20. Cool to 40° C. and seed with 0.1 wt % Compound 6.
21. Cool slowly to 5° C.
22. Hold for at least 2 hours.
23. Filter and wash the cake with two 1.35 kg volume portions of 50:50 EtOH:H$_2$O (1.2 kg EtOH combined with 1.5 kg H$_2$O).
24. Dry the cake at less than 50° C.

Example 8

Preparation of a Compound of Formula 9a

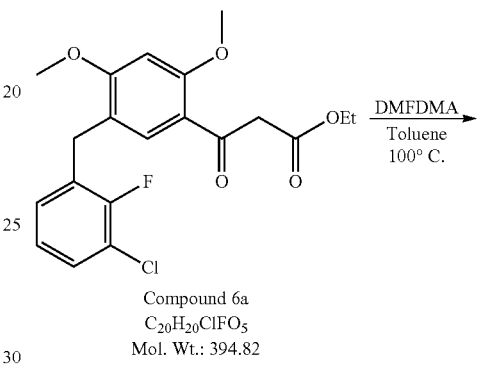

Compound 6a
C$_{20}$H$_{20}$ClFO$_5$
Mol. Wt.: 394.82

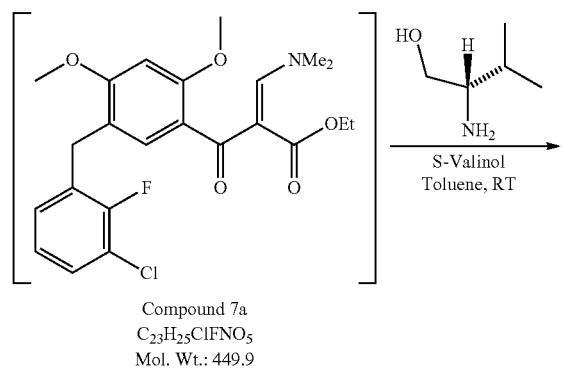

Compound 7a
C$_{23}$H$_{25}$ClFNO$_5$
Mol. Wt.: 449.9

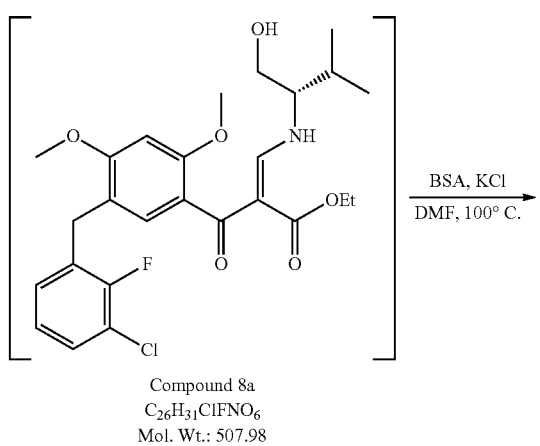

Compound 8a
C$_{26}$H$_{31}$ClFNO$_6$
Mol. Wt.: 507.98

-continued

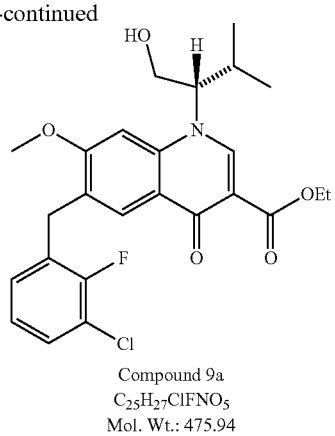

Compound 9a
$C_{25}H_{27}ClFNO_5$
Mol. Wt.: 475.94

Compound 6a is combined with toluene, N,N-dimethylformamide dimethyl acetal and glacial acetic acid before being warmed to 100° C. The reaction is monitored by HPLC. Once the formation of Compound 7a is complete the mixture is cooled to 18 to 25° C. before (S)-(+)-valinol is added. The reaction is monitored by HPLC. Once the formation of Compound 8a is complete the mixture is concentrated. The residue is combined with dimethylformamide, potassium chloride and N,O-bistrimethylsilyl acetamide and warmed to 100° C. The reaction is monitored by HPLC. Once complete the mixture is cooled and dichloromethane is added. Aqueous hydrochloric acid is added to desilylate Compound 9a. This reaction is monitored by TLC. Once complete the organic phase is washed with water, aqueous sodium bicarbonate and water. The solvent is exchanged for acetonitrile and the mixture warmed. The mixture is seeded and cooled to crystallize Compound 9a. The product is filtered, washed with cold acetonitrile and dried at NMT 40° C. to yield Compound 9a.

| Material | M.W. | Wt. Ratio | Mole Ratio |
|---|---|---|---|
| Compound 6a | 394.82 | 1.00 | 1.00 |
| Toluene | 92.14 | 4.3 | |
| Glacial acetic acid | 60.05 | 0.001 | 0.007 |
| N,N-dimethylformamide dimethyl acetal | 119.16 | 0.33 | 1.1 |
| (S)-(+)-Valinol | 103.16 | 0.29 | 1.1 |
| DMF | 73.10 | 1.8 | |
| KCl | 74.55 | 0.09 | 0.5 |
| N,O-bis(trimethylsilyl)acetamide | 203.43 | 1.13 | 2.2 |
| 1N HCl | 36.5 | 2.0 | |
| DCM | 84.93 | 10 | |
| Water | 18.02 | 8 | |
| 5% Aq. NaHCO$_3$ | 84.01 | 4 | |
| CAN | 41.05 | QS | |
| Compound 9a seeds | 475.94 | 0.005 | |

1. Charge Reactor 1 with 1.00 kg Compound 6a.
2. Charge 0.33 kg N,N-dimethylformamide dimethyl acetal (1.1 eq), 0.001 kg glacial acetic acid and 3.3 kg toluene to Reactor 1.
3. Warm the mixture to ~100° C. (note that some MeOH may distill during this operation).
4. After 1 h the reaction should be complete by HPLC (~2% Compound 6a apparently remaining)[1].
5. Cool the mixture in Reactor 1 to 18-25° C.
6. Charge 0.29 kg (S)-(+)-Valinol (1.1 eq) dissolved in 1.0 kg toluene to Reactor 1 and continue agitation at ambient temperature.
7. After 1 h the reaction should be complete by HPLC (<1% Compound 6a).
8. Concentrate the contents of Reactor 1 to ~2 L/kg.
9. Charge 1.8 kg DMF, 0.09 kg potassium chloride (0.5 eq.) and 1.13 kg N,O-bistrimethylsilyl acetamide (2.2 eq.) to Reactor 1.
10. Warm the mixture in Reactor 1 to ~100° C.
11. Reaction should be complete in ~1 h (~5% Compound 8a remaining)
12. Cool the contents of Reactor 1 to 18-25° C.
13. Charge 10 kg DCM to Reactor 1.
14. Charge 2.0 kg 1 N aqueous HCl to Reactor 1 over ~15 min, maintaining the temperature of the mixture <35° C.
15. Agitate the mixture for at least 10 min to desilylate Compound 8a. Monitor the progress of desilylation by TLC.[2]
16. Separate the phases.
17. Wash the organic phase with 4.0 kg water.
18. Wash the organic phase with 4.0 kg 5% aqueous sodium bicarbonate.
19. Wash the organic phase with 4.0 kg water.
20. Concentrate the organic phase by distillation to ~1.5 L/kg Compound 6a.
21. Solvent exchange to ACN by distillation until a slurry is formed. Adjust the final volume to ~8 L/kg Compound 6a.
22. Heat the mixture to reflux to redissolve the solid.
23. Cool the solution to 75° C. and charge Compound 9a seeds.
24. Cool the mixture to 0° C. over at least 2 h and hold at that temperature for at least 1 h.
25. Isolate Compound 9a by filtration and wash the wet cake with 1.6 kg cold ACN.
26. Dry the wet cake at <40° C. under vacuum.

Notes:
1. The HPLC AN of remaining Compound 6a is exaggerated by a baseline artifact. The HPLC in step shows only 2% of Compound 6a relative to Compound 8a. Experiments demonstrated that adding more reagent and extending reaction time typically will not further reduce the observed level of Compound 6a.
2. TLC method:
   Eluting solvent: 100% ethyl acetate,
   Silylated Compound 9a Rf: 0.85, Compound 9a Rf: 0.50.

Example 9

Preparation of a Compound of Formula 10

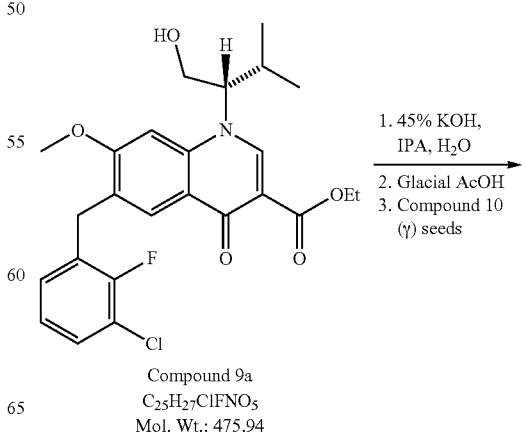

Compound 9a
$C_{25}H_{27}ClFNO_5$
Mol. Wt.: 475.94

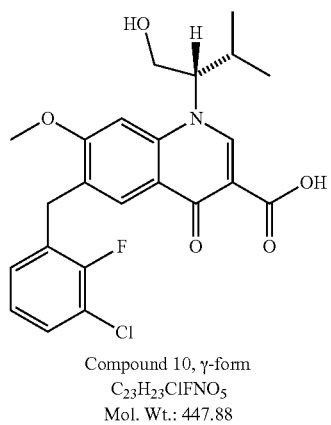

Compound 10, γ-form
$C_{23}H_{23}ClFNO_5$
Mol. Wt.: 447.88

Compound 9a is combined with aqueous isopropyl alcohol and warmed to 30 to 40° C. Aqueous potassium hydroxide is added and the reaction is monitored by HPLC. Once complete, glacial acetic acid is added and the mixture warmed to 60 to 70° C. The solution is hot filtered and cooled to 55 to 65° C. The solution is seeded (see International Patent Application Publication Number WO 2005/113508) and cooled to 0° C. The product is isolated by filtration, washed with cold aqueous isopropyl alcohol and dried at NMT 50° C. to yield Compound 10.

| Material | M.W. | Wt. Ratio | Mole Ratio |
|---|---|---|---|
| Compound 9a | 475.94 | 1.00 | 1.00 |
| Isopropyl alcohol | 60.10 | 4.7 | |
| Water | 18.02 | 4.0 | |
| 45% KOH | 56.11 | 0.34 | 1.3 |
| Glacial Acetic Acid | 60.05 | 0.19 | 1.50 |
| Compound 10 seeds | 447.88 | 0.01 | |

1. Charge 1.00 kg Compound 9a to Reactor 1.
2. Charge 4.7 kg isopropyl alcohol and 4.0 kg water to Reactor 1.
3. Charge 0.34 kg 45% aqueous KOH to Reactor 1.
4. Warm the mixture in Reactor 1 to 30-40° C.
5. When hydrolysis is complete add 0.19 kg of glacial acetic acid.
6. Warm the mixture to 60-70° C. and polish filter the solution to Reactor 2.
7. Cool the mixture in Reactor 2 to 55-65° C.
8. Seed with Compound 10 (see International Patent Application Publication Number WO 2005/113508) as a slurry in 0.28 volumes of 6:4 isopropyl alcohol:water.
9. Cool the mixture to 18-25° C. over at least 2 h and agitate to form a slurry.
10. Cool the mixture to 0° C. and agitate for at least 2 h.
11. Isolate Compound 10 by filtration and wash the cake with 3×1 S cold isopropyl alcohol:water (6:4) solution.
12. Dry the isolated solids at <50° C. under vacuum.

Example 10

Preparation of Compound 15

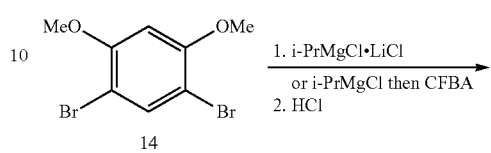

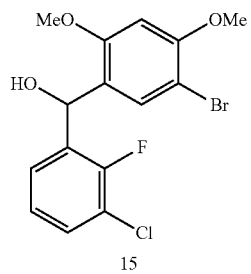

15

Bisdimethylaminoethyl ether (2.84 g) was dissolved in 42 mL THF and cooled in an ice bath. Isopropylmagnesium chloride (8.9 mL of a 2 M solution in THF) followed by Compound 14 (5 g dissolved in 5 mL THF) were added slowly sequentially. The mixture was allowed to warm to ambient temperature and stirred overnight. Next, 2.1 mL of 3-chloro-2-fluorobenzaldehyde was added. After stirring for ~1 h, the mixture was quenched to pH ~7 with 2N HCl. The product is extracted into ethyl acetate and the organic phase was dried over sodium sulfate. The solvent was exchange to heptane to precipitate the product and a mixture of heptanes: MTBE (4:1) was added to form a slurry. After filtration the solid was slurried in toluene, filtered and vacuum dried to yield compound 15: $^1$H NMR (CD$_3$CN, 400 MHz) δ 7.47 (s, 1H), 7.41-7.35 (m, 2H), 7.15 (t, J=7.4 Hz, 1H), 6.66 (s, 1H), 6.21 (br s, 1H), 3.90 (s, 3H), 3.87 (br s, 1H), 3.81 (s, 3H).

Example 11

Preparation of Compound 15a

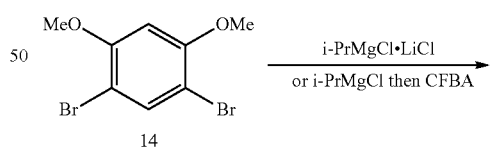

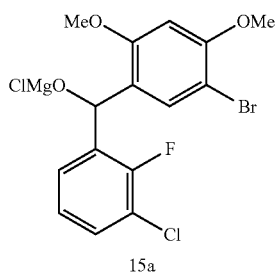

15a

Compound 14 (5 g), isopropylmagnesium chloride (8.9 mL of 2M solution in THF) and THF (56 mL) were combined at ambient temperature and then warmed to 50° C. for ~5 hours. After cooling to ambient temperature and stirring overnight, 2.1 mL of 3-chloro-2-fluorobenzaldehyde was added dropwise to form a slurry. After stirring overnight the solid was isolated by filtration and washing with MTBE to yield compound 15a.

Example 12

Preparation of Compound 16

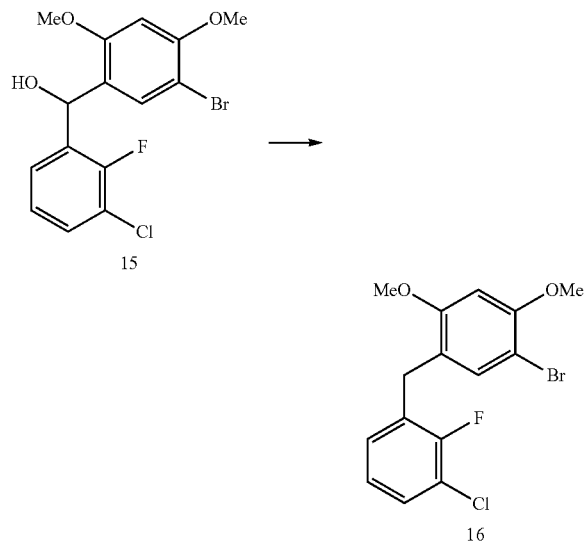

Triethylsilane (1.2 mL) was added to trifluoroacetic acid (2.3 mL) that had been pre-cooled in an ice bath. Compound 15 (1.466 g) was added to the mixture keeping the temperature below 5° C. After stirring for ~2 h ice was added to quench the reaction. The product was extracted with DCM and the organic phase was washed with aq. NaHCO$_3$. The organic phase was dried over Na$_2$SO$_4$ and concentrated to dryness. The product was purified by silica gel column chromatography to provide 1.341 g of Compound 16: $^1$H NMR (CDCl$_3$, 400 MHz) δ 7.20 (t, J=7.0 Hz, 1H), 6.99-6.91 (m, 3H), 6.46 (s, 1H), 3.91 (s, 3H), 3.81 (s, 5H).

The compound of formula 16 can be carboxylated to provide a compound of Formula 4 following a method analogous to that described in Example 1.

Example 13

Alternative Preparation of a Compound of Formula 3

Compound 14 is combined with anhydrous tetrahydrofuran:dioxane (5:0.9), and the mixture is agitated under a nitrogen atmosphere until a homogeneous solution is achieved. The solution is cooled to −3° C. and 1.3 eq. of i-PrMgCl.LiCl in tetrahydrofuran is added. The reaction mixture is agitated at 0° C. until the formation of the mono-Grignard is complete as determined by HPLC analysis. Next, a solution of 1.1 eq. of 3-chloro-2-fluorobenzaldehyde in tetrahydrofuran is added. This mixture is allowed to stir at 0° C. until the formation of Compound 15a is complete by HPLC. Next, additional i-PrMgCl.LiCl solution in tetrahydrofuran (2.5 eq.) is added and the reaction mixture is warmed to about 20° C. After conversion to the second Grignard intermediate is complete, the reaction mixture is cooled to 3° C. Anhydrous CO$_2$ (g) is charged to the reaction mixture at about 5° C. The reaction mixture is adjusted to about 20° C. After the carboxylation reaction is complete by HPLC, the reaction mixture is cooled to about 10° C. and water is charged to quench the reaction followed by the addition of concentrated hydrochloric acid to adjust the pH to no more than 3. The reaction mixture is then warmed to about 20° C. The phases are separated. The organic phase is solvent exchanged to a mixture of isopropyl alcohol and water and the resulting slurry is cooled to about 0° C. The product is isolated by filtration, washed with a mixture of isopropyl alcohol and water and dried at about 40° C. to yield Compound 3.

Example 14

Alternative Preparation of Compound of Formula 4

Trifluoroacetic acid (10 eq.) is charged to a reactor and cooled to 0° C. Triethylsilane (1.5 eq.) is added maintaining the temperature <15° C. and the mixture agitated thoroughly. Compound 3 is added to the well-stirred mixture in portions maintaining the temperature <15° C. When the reaction is determined to be complete by HPLC, Compound 4 is precipitated by adding a solution of 5 eq. sodium acetate in methanol (13 volumes) maintaining the temperature not more than 45° C. Warm the slurry to reflux and agitate for 2 to 3 h. The slurry is cooled to about 0° C. and then agitated at that temperature for 2 to 3 h. The product is isolated by filtration, washed with methanol and dried at about 40° C. to yield Compound 4.

Example 15

Alternative Preparation of a Compound of Formula 9a

Compound 6a is combined with dimethylformamide (1.9 vol.), N,N-dimethylformamide dimethyl acetal (1.1 eq.) and glacial acetic acid (0.026 eq.) before being warmed to about 65° C. The reaction is monitored by HPLC. Once the reaction is complete the mixture is cooled to about 22° C. before (S)-2-amino-3-methyl-1-butanol (1.1 eq.) and toluene (1.2 volumes) are added. The reaction is monitored by HPLC. Once the reaction is complete the mixture is concentrated. The residue is combined with potassium chloride (0.5 eq) and N,O-bis(trimethylsilyl)acetamide (2.5 eq.) and warmed to about 100° C. The reaction is monitored by HPLC. Once the reaction is complete the mixture is cooled and dichloromethane (6 vol.) is added. Aqueous hydrochloric acid is added to desilylate the product. This reaction is monitored by TLC. Once the reaction is complete the organic phase is washed with water, aqueous sodium bicarbonate and water. The solvent is exchanged for acetonitrile and the mixture is warmed to form a solution. The mixture is seeded and cooled to crystallize Compound 9a. The product is filtered, washed with cold acetonitrile and dried at NMT 40° C. to yield Compound 9a.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for preparing a compound of formula 4

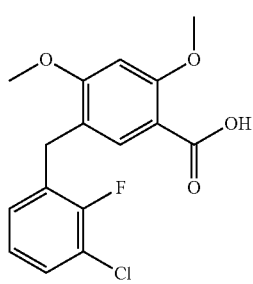

4 or a salt thereof from a compound of formula 15

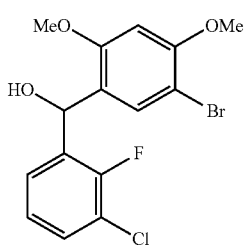

15 or a salt thereof, by the steps of replacing the bromine atom with a carboxyl group, and replacing the hydroxyl group with a hydrogen atom.

2. A method of claim 1, wherein the compound of formula 4 or a salt thereof is prepared by metalating the compound of formula 15 or a salt thereof and treating with carbon dioxide to provide the compound of formula 3:

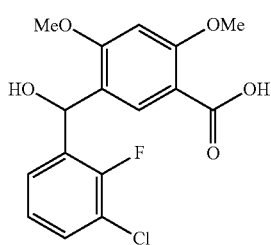

3 or a salt thereof, and converting the compound of formula 3 to provide the compound of formula 4.

3. A method of claim 2, wherein the compound of formula 15 or a salt thereof is a salt of formula 15a

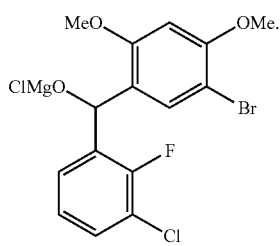

15a

4. A method of claim 1, wherein the compound of formula 15 is converted into a compound of formula 16

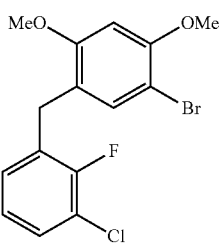

16 by replacing the hydroxyl group with a hydrogen atom to provide the compound of formula 16 which is then metalated and treated with carbon dioxide to afford a compound of formula 4.

5. A method for preparing a compound of formula 10

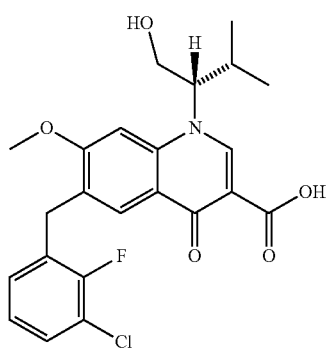

10 comprising converting a compound of formula 15

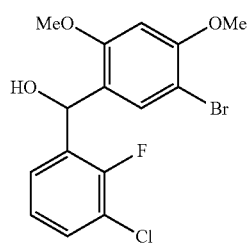

15 or a salt thereof to a compound of formula 3:

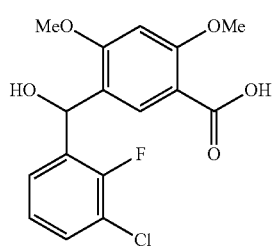

3 or the salt thereof;
converting a compound of formula 3 or the salt thereof to a compound of formula 4:

4

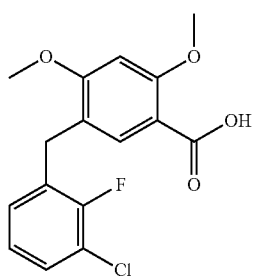

or a salt thereof;
converting the compound of formula 4 or the salt thereof to a compound of formula 5':

5'

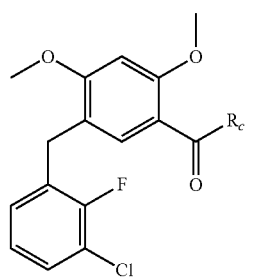

or a salt thereof, wherein $R_c$ is a leaving group;
converting the compound of formula 5' or a salt thereof, to a compound of formula 6:

6

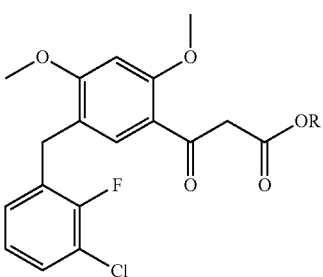

or a salt thereof, wherein R is $C_1$-$C_6$alkyl;
converting the compound of formula 6 or a salt thereof, to a compound of formula 7:

7

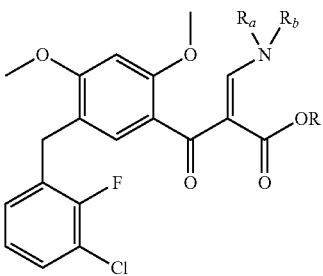

wherein $R_a$ and $R_b$ are each independently $C_1$-$C_6$alkyl;

converting the compound of formula 7 to a compound of formula 8:

8

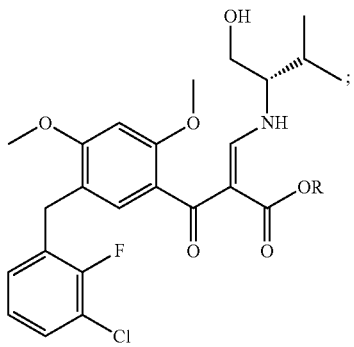

converting the compound of formula 8 to a compound of formula 9:

9

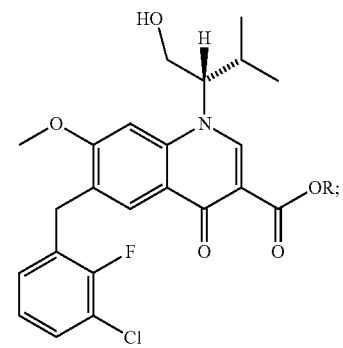

and
converting the compound of formula 9 to a compound of formula 10:

10

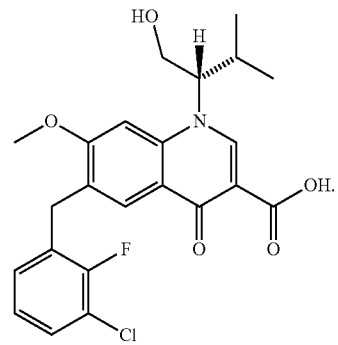

6. A method for preparing a compound of formula 3:
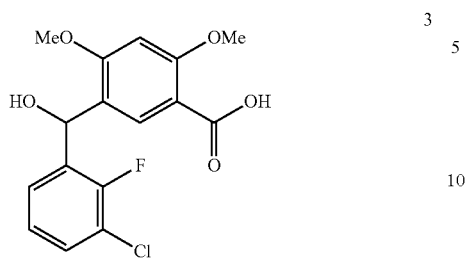
3
or a salt thereof, wherein a compound of formula 15:
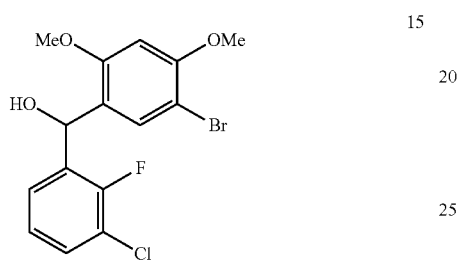
15
is converted to the compound of formula 3 by metalating the compound of formula 15 and treating with carbon dioxide to provide the compound of formula 3.
* * * * *